US010888457B2

(12) United States Patent
Artsyukhovich

(10) Patent No.: US 10,888,457 B2
(45) Date of Patent: Jan. 12, 2021

(54) DETACHABLE MINIATURE MICROSCOPE MOUNTED KERATOMETER FOR CATARACT SURGERY

(71) Applicant: Alex Artsyukhovich, Irvine, CA (US)

(72) Inventor: Alex Artsyukhovich, Irvine, CA (US)

( * ) Notice: Subject to any disclaimer, the term of this patent is extended or adjusted under 35 U.S.C. 154(b) by 239 days.

(21) Appl. No.: 16/095,897

(22) PCT Filed: Apr. 19, 2017

(86) PCT No.: PCT/US2017/028215
§ 371 (c)(1),
(2) Date: Oct. 23, 2018

(87) PCT Pub. No.: WO2017/189283
PCT Pub. Date: Nov. 2, 2017

(65) Prior Publication Data
US 2019/0167474 A1    Jun. 6, 2019

Related U.S. Application Data

(60) Provisional application No. 62/391,343, filed on Apr. 28, 2016.

(51) Int. Cl.
| *A61B 3/10* | (2006.01) |
| *A61B 3/14* | (2006.01) |
| *A61B 3/02* | (2006.01) |
| *A61B 3/00* | (2006.01) |
(Continued)

(52) U.S. Cl.
CPC ........ *A61F 9/00736* (2013.01); *A61B 3/0091* (2013.01); *A61B 3/102* (2013.01);
(Continued)

(58) Field of Classification Search
CPC .......... A61B 3/107; A61B 3/103; A61B 3/14; A61B 3/113; A61B 3/1225; A61B 3/024; A61B 3/032; A61B 3/18; A61B 3/1015
(Continued)

(56) References Cited

U.S. PATENT DOCUMENTS

| 4,597,648 A | 7/1986 | Feldon et al. |
| 5,312,393 A | 5/1994 | Mastel |
(Continued)

FOREIGN PATENT DOCUMENTS

| CN | 2574592 Y | 9/2003 |
| WO | 2016061454 A1 | 4/2016 |

OTHER PUBLICATIONS

Mas et al., "Custom designed dynamic videokeratometer." Journal of Modern Optics. 2009 (2009), pp. 2-7.

*Primary Examiner* — Dawayne Pinkney
(74) *Attorney, Agent, or Firm* — SZDC Law P.C.

(57) ABSTRACT

A keratometer for intra-surgery measurements mounted under a surgical microscope includes a Placido ring illuminating a patient's eye; a video camera; a beamsplitter directing a Purkinje image of the Placido ring to the video camera; a fixation light directing a beam for patient eye fixation, fixation confirmation or creating a red reflex effect to enhance IOL imaging and cataract visualization; a processor configured to determine the refractive characteristics and keratometer parameters of the patient's eye and to execute a digital image enhancement method to outline IOL features to help IOL alignment; and a digital display displaying the keratometer parameters and surgical guidance information for a surgeon.

20 Claims, 7 Drawing Sheets

(51) Int. Cl.
- *A61F 9/007* (2006.01)
- *A61B 3/107* (2006.01)
- *A61B 3/13* (2006.01)
- *A61F 2/16* (2006.01)
- *A61B 3/036* (2006.01)
- *A61B 90/00* (2016.01)

(52) U.S. Cl.
CPC ............... *A61B 3/107* (2013.01); *A61B 3/13* (2013.01); *A61B 3/145* (2013.01); *A61F 2/1662* (2013.01); *A61B 3/036* (2013.01); *A61B 2090/3735* (2016.02)

(58) Field of Classification Search
USPC ....... 351/212, 200, 205, 206, 210, 221–223, 351/209, 245–246
See application file for complete search history.

(56) References Cited

U.S. PATENT DOCUMENTS

| | | |
|---|---|---|
| 5,735,283 A | 4/1998 | Snook |
| 2001/0055095 A1 | 12/2001 | D'Souza et al. |
| 2005/0203492 A1 | 9/2005 | Nguyen et al. |
| 2006/0028619 A1 | 2/2006 | Fujieda et al. |
| 2010/0217278 A1 | 8/2010 | Tripathi |
| 2011/0242483 A1 | 10/2011 | Shea et al. |
| 2014/0063455 A1* | 3/2014 | Zhou .................. G01J 9/00 351/206 |
| 2014/0249624 A1 | 9/2014 | Ianchulev |
| 2016/0074125 A1 | 3/2016 | Raymond et al. |
| 2016/0095752 A1 | 4/2016 | Srinivasan et al. |
| 2016/0227996 A1* | 8/2016 | Neal .................. A61B 3/0025 |

* cited by examiner

F1     F2     F3

DETACHABLE MINIATURE MICROSCOPE MOUNTED KERATOMETER FOR CATARACT SURGERY

This application is the national stage application of PCT/US2017/028215, filed on Apr. 19, 2017, which claims priority to U.S. Provisional Application No. 62/391,343, filed Apr. 28, 2016, which is incorporated by reference for all purposes as if fully set forth herein.

FIELD OF THE INVENTION

The present invention relates to a diagnostic instrument and its application, more particularly, to a detachable keratometer for intra-surgery measurements mounted under a surgical microscope and a method of using the same.

BACKGROUND OF THE INVENTION

Cataract surgery is #1 in volume surgery in the World. Currently there are 3 million cataract surgeries performed each year in US. Western Europe also performs 3 million cataract surgeries. The WHO estimates that by 2020, 32 million cataract surgeries will be performed, up from 12 million in 2000. This is not just due to increased life span and baby boomer demographic population increase. More people using digital devices (tablets, smart phones) and continuing to lead active lifestyle in the retirement. As such more people elect to perform cataract surgery and have functional vision.

Cataract surgery is a process that extracts cataractous (opaque) lens from patient's eye and replaces it with an artificial intra-ocular lens (IOL). To prescribe intra-ocular lens implant a number of ocular measurements (biometry) are currently done prior to surgery for best vision outcome. Critical parameters like eye axial length, corneal radii, and anterior chamber depth are measured. Currently insufficient accuracy of biometry results in poor cataract surgery outcomes 50% of the time, when patients have >0.5 Diopter Refractive error surgical outcome and need to wear glasses after surgery. The lack of tools for intraoperative astigmatism measurement slows down adoption of toric IOLs that correct astigmatism.

When light reflects from human eye there are four reflections, known as Purkinje images 1-4, coming from anterior cornea (Purkinje 1 image), posterior cornea (Purkinje 2 image), anterior lens (Purkinje 3 image) and posterior lens (Purkinje 4 image). Measuring of radii of corneal curvature (Ks) is traditionally based on a well-known Placido keratometry technology first described by Placido in 1880 in an article "a novo instrumiento par analyze immediate das irregularidades de curvature de cornea," Periodico Ophthalmol Practica 1880: 6: 44-49. Placido ring reflection from anterior cornea (Purkinje image 1) is analyzed to extract corneal curvature information.

U.S. Pat. No. 4,046,463 gives a design of Placido rings based keratometer that is mounted under surgical microscope. The rings shapes are measured via visual comparison with reticle. This keratometer allows measuring Sphere, Cylinder and Angle of anterior corneal shape by measuring parameters of elliptic Purkinje-1 image of Placido ring, formed by a ring of light sources located under microscope's objective and above patient's eye.

U.S. Pat. No. 4,597,648 describes compact microscope mounted keratometer that uses linear video sensor with scanning optics to capture image of Placido rings, reflected from cornea. The ring image is produced by a circle of light sources (fiber-optical and LED) mounted on the bottom side of keratometer. The image is digitized and processed by a computer processor. The surgeon is informed live during surgery about astigmatism axis angle via a live video image of an eye on a video monitor with digitally superimposed line, designating astigmatism angle. Moreover, the two LEDs closest to astigmatism angle on a keratometer ring are lit by a processor to produce two bright dots on patient's cornea, designating astigmatism angle. U.S. Pat. No. 5,307,096 suggests that computer, analyzing Placido ring Purkinje 1 image, should display an image, representing shape of the cornea. U.S. Pat. No. 5,349,398 suggests that such image be topography map displayed concurrently with surgical operation on the eye. It suggests a number of different forms of intra-operative information display, e.g. (1) a video display of corneal contour, (2) a digital readout of spherical curvature, astigmatism, asphericity, etc., and/or (3) suggested surgical steps to correct the observed errors in corneal shape. It also suggests surgeon making adjustments the sutures to correct the asphericity of cornea.

U.S. Pat. No. 4,660,946 describes similar system for a table-top keratometer for patient's office visits. It is based on a CCD video registration and grabs Placido ring image in one frame. Computer is then used to process digitized image for cornea radii.

One difficulty is to apply pre-surgery biometry that is normally done two weeks before surgery to intra-surgery guidance. This is especially true for transferring astigmatism angle orientation for toric IOL alignment. A number of methods using video and image registration were developed to transfer astigmatism angle, measured during office visit, into intra-surgery guidance. This is because due to cyclotorsion an eye of a patient on surgical table rotates with respect to visual axis from its orientation in sitting patient during an office visit. One way is to snap an image of patient scleral blood vessels during office visit and later use them as landmarks for registering image of patient eye intra-surgery (see, e.g., U.S. Pat. Nos. 7,905,887 and 8,414,123). The extra step of image registration adds here an error to original pre-operative astigmatism angle measurement. Also it is unable to accurately account for Surgically Induced Astigmatism (SIA) created post-measurement due to corneal incisions during surgery. A better way is to perform refractive measurement right there during surgery, bypassing the need of pre-operative to intra-operative eye image registration with its registration error and fully accounting for SIA (See, e.g., U.S. Pat. Nos. 7,988,291 and 8,882,270). These are very complex and expensive optical devices that are large in size and take up to 30% of surgical space under microscope during cataract micro-surgery.

Despite many historical designs of keratometers—all of them have been developed into office based devices, in which patient and doctor sit at the table, facing each other and having table top keratometer located between them. Several microscope-mounted keratometers were proposed, but none of them has been realized in commercial product. This is due to the difficulty of achieving high accuracy in a small microscope-mounted device—the device's size is restricted by surgical space available. Thus, there is a need for a miniature detachable microscope-mounted keratometer for live intra-surgery keratometry.

SUMMARY OF THE INVENTION

In one embodiment, the present invention provides a keratometer for intra-surgery measurements mounted under a surgical microscope. The keratometer includes a Placido ring illuminating a patient's eye; a video camera; a beamsplitter directing a Purkinje image of the Placido ring to the video camera; a fixation light directing a beam for patient eye fixation, fixation confirmation or creating a red reflex effect to enhance IOL imaging and cataract visualization; a processor configured to determine the refractive characteristics and keratometer parameters of the patient's eye and to execute a digital image enhancement method to outline IOL features to help IOL alignment; and a digital display displaying the keratometer parameters and surgical guidance information for a surgeon.

In another embodiment, the Placido ring is configured to flash with a frames-per-second rate of the video camera and to skip flashing for at least one frame for background recording and subtraction.

In another embodiment, 0.02-30% of the Purkinje image is defined as a small Region-of-Interest window and is used to extract information out of the Purkinje image for high frames-per-second measurement and averaging.

In another embodiment, the keratometer further includes a fixation detector. The fixation light is an integrated fixation near-collimated visible or NIR light source pulsating at 0.5 Hz-1 MHz frequency; and the fixation detector confirms patient compliance and accepts measurements with correct fixation.

In another embodiment, the keratometer further includes an integrated optical coherence tomography scanner. The integrated optical coherence tomography scanner extracts information on posterior corneal surface curvature, anterior chamber depth and IOL location.

In another embodiment, digital display is integrated into the keratometer as a digital overlay display.

In another embodiment, the near-collimated visible or NIR light source, when operated in a constant "ON" mode, creates a fundus reflection effect for video contrast.

In another embodiment, the digital image enhancement method is applied to live video to outline IOL features for IOL alignment ease.

In another embodiment, different optical channels of the Placido ring, the fixation light, the fixation detector and the Purkinje image are separated spectrally for a coaxial operation.

In another embodiment, an angular offset in degrees is applied to compensate for difference between anterior corneal astigmatism and total cornea astigmatism, and combining anterior and posterior corneal astigmatism is applied in GUI.

In one embodiment, the present invention provides a keratometry method. The method includes receiving, from a video camera of a keratometer mounted under a surgical microscope, Purkinje images and a background image of a patient's eye by properly controlling a Placido ring and a fixation light; executing, by a processor, an analytic software to determine refractive characteristics and keratometer parameters of the patient's eye based on the Purkinje images and background image and a digital image enhancement method to outline IOL features to assist IOL alignment; and displaying live lines over image of the patient's eye indicating a determined astigmatism angle of the eye.

In another embodiment, the Placido ring flashes with a frames-per-second rate of the video camera and skips flashing for at least one frame for background recording and subtraction.

In another embodiment, different optical channels are separated spectrally for a coaxial operation.

In another embodiment, the keratometry method further includes providing an integrated fixation collimated visible or NIR light source pulsating at 0.5 Hz-1 MHz frequency and a fixation detector to confirm patient compliance; and accepting measurements with correct fixation.

In another embodiment, the keratometry method further includes using Purkinje 1, 2, 3 and 4 images and/or integrated an optical coherence tomography scanner to extract information on posterior corneal surface curvature, anterior chamber depth and IOL location.

In another embodiment, the keratometry method further includes using precision diameter balls of known sizes for calibration.

In another embodiment, the analytic software is configured to calculate an astigmatism angle by offsetting to account for a pre-op total cornea astigmatism angle delta.

In another embodiment, the keratometry method further includes providing a near-collimated visible or NIR light source to fix the patient's eye and creating a red reflex effect enhancing the contrast of an IOL or assisting cataract visualization.

In another embodiment, the refractive characteristics and the live lines are displayed in a tablet PC, an external display attachable on the surgical microscope, or a digital display integrated with the keratometer injecting digital overlay into a surgeon's intra-operative view.

In another embodiment, the analytic software applies a Fast Fourier Transformation to analyze the Purkinje image for ellipse parameters extraction.

In another embodiment, the keratometry method further includes applying 0.02-30% of the Purkinje images captured by the video camera for high frames-per-second measurements and averaging.

In another embodiment, the keratometry method further includes the following steps: pre-operative biometry, keratometer calibration, cataractous lens surgical removal, eye preparation for intra-operative keratometry, microscope centration, microscope height adjustment, LEDs brightness adjustment, achieving patient's fixation, keratometry measurement, displaying astigmatism line, and toric IOL implantation and alignment.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

DETAILED DESCRIPTION OF THE ILLUSTRATED EMBODIMENTS

Reference will now be made in detail to embodiments of the present invention, example of which is illustrated in the accompanying drawings.

Figure 1:
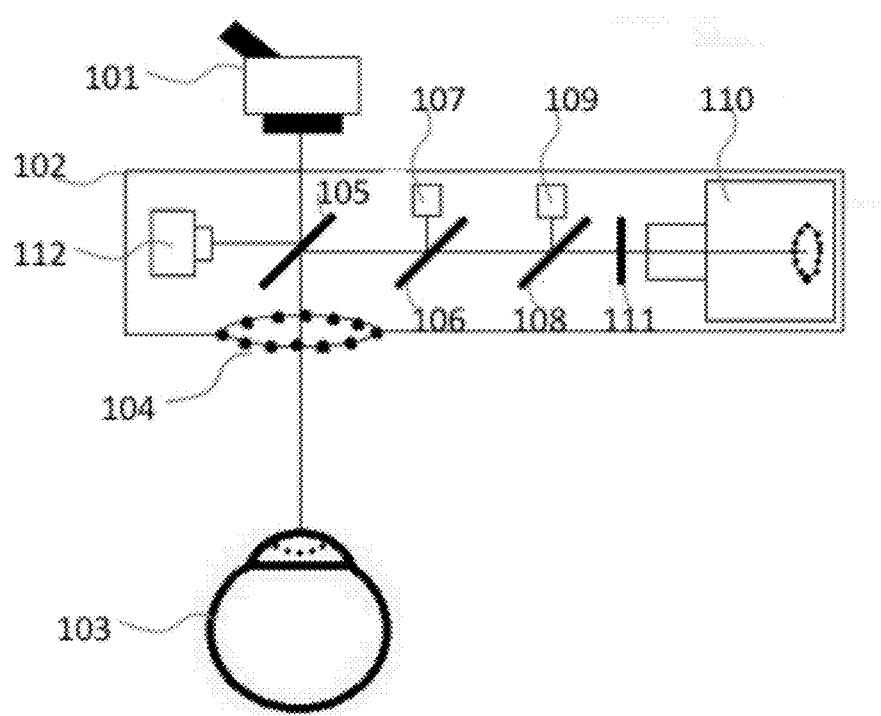
FIG. 1 depicts schematically one detachable keratometer according to one embodiment of the present invention: 101—surgical microscope; 102—detachable keratometer; 103 procedure eye; 104—Placido ring light source; 105, 106 and 108—Beamsplitter; 107—fixation light; 109—fixation detector; 110—keratometer video camera with objective lens; 111—optical filter; 112—digital display with lens.

FIG. 1 depicts schematically one proposed implementation of suggested detachable miniature keratometer device. A surgical microscope 101 has the keratometer device 102 attached at the bottom of it—above a patient's eye 103. The keratometer device 102 has an illuminated Placido ring 104 (or multiple Placido rings) attached at the bottom. FIG. 1 shows it as a ring formed by 12 discrete light sources—LEDs. But one skilled in art recognizes that other means of Placido ring can be utilized—a continuous illuminated ring based on fiber optics or scattering optical material. The number of discrete light sources can be changed. One or multiple Placido rings can be projected by using a projection lens and OLED display or reticle, illuminated with light source. A Purkinje-1 image of Placido ring 104 formed on anterior cornea of the patient's eye 103 is then reflected by a Beamsplitter 105 to a video camera 110. The video camera 110 has an objective lens integrated and has an optical filter 111 in front of the objective lens to reduce background light. Beamsplitter 106 is used to reflect light from a blinking fixation light 107—LED or other. Beamsplitter 108 is used to couple an image of the patient's eye 103 to a fixation detector 109—a device that confirms patient compliance with fixation request, or so-called fixation confirmation. The digital display 112 is designed to inject digital graphics into a surgeon's intra-operative view of operative field through a lens system. It can be based on OLED, LCD, DLP, LCOS, or other display and projection technologies. Although FIG. 1 shows the keratometer device 102 being attached to the microscope 101, the device can also be mounted as table top. Table top system can be useful for ophthalmic office-based system where the surgical planning is performed. The video information from the video camera 110 is then fed to a processor or a tablet PC (not shown in FIG. 1) to determine the refractive characteristics and keratometer parameters of the patient's eye. The tablet PC or a separate display/monitor is mounted to the surgical microscope 101 or other stand.

Figure 2:
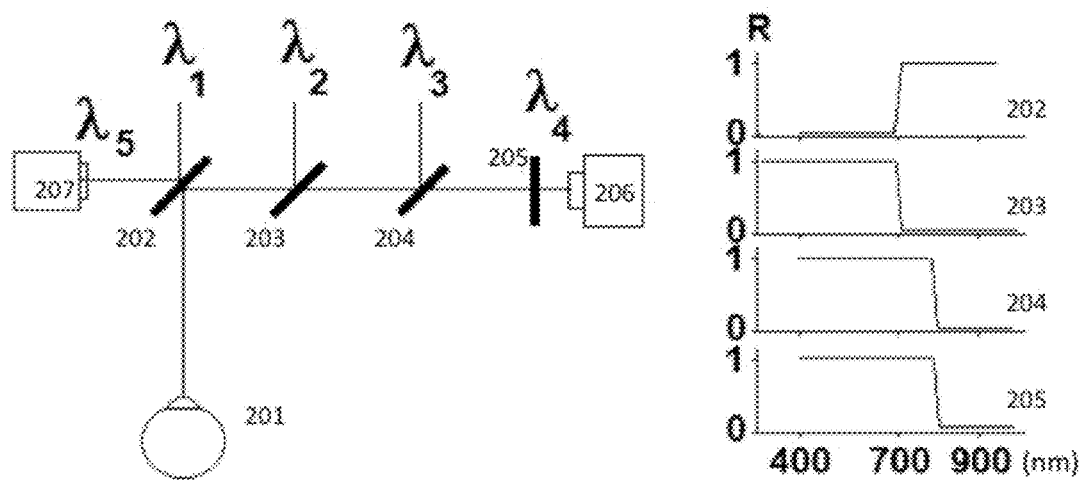
FIG. 2 depicts the spectral separation of detachable keratometer optical channels: $\lambda 1$=420-650 nm; $\lambda 2$=560 nm; 23=750 nm; $\lambda 4$=875 nm; $\lambda 5$=660 nm; 201—patient's eye; 202-204—optical beamsplitters; 205—optical filter; 206—video camera; 207—digital display with lens. On the right there are schematic reflection spectra of optical elements 202-205 depicted for current implementation.

In FIG. 1, a number of optical components/devices are operating in a coaxial way. The surgical microscope 101 visual and illumination paths coincide with optical paths to the camera 110, fixation light 107 and fixation detector 109. Clearly one can use spectral differences to achieve separation of different optical channels. FIG. 2 is depicting four spectral separation elements of such implementation—beamsplitters 202, 203, 204 and optical filter 205. Patient's eye 201 is viewed by the surgeon through beamsplitter 202 in the full visible range of wavelength designated here as $\lambda_1$. A pulsating light of fixation source could be any visible wavelength $\lambda_2$, but preferably red for high visibility. The light is pulsating for ease of finding and fixating on it, when patient is illuminated with microscope light at the same time. The characteristic pulsation rate should be anywhere from 0.5 Hz to 15 Hz, 1 Hz to 10 Hz, or 0.5 Hz to 1 MHz to be noticeable. The fixation light is reflected by beamsplitter 203 and beamsplitter 202. Beamsplitter 202 is designed to transmit full visible range (or near full) for proper microscope function, but at 45 degree angle the residual reflection coefficient for fixation light wavelength $\lambda_2$ is sufficient. The beamsplitter 204 is designed to reflect fixation detection wavelength $\lambda_3$ and transmit Placido ring source wavelength $\lambda_4$. Optical filter 205 is designed to transmit $\lambda_4$ and block all other wavelengths to prevent background light interference. And lastly, beamsplitter 202 can be used as well for reflecting upwards the image of digital display 112 at wavelength $\lambda_5$. Such digital display can be used to superimpose digital signs and text over surgeon's view of operative field. For example a digital line can be projected to designate astigmatism angle. Various wavelength combinations can be used. Infra-Red radiation can be used for Placido ring illumination to make it invisible to the patient. One of the proposed implementations has the following set of wavelengths: $\lambda_1$=420-635 nm; $\lambda_2$=560 nm; $\lambda_3$=750 nm; $\lambda_4$=850 nm and $\lambda_5$=635 nm. FIG. 2 also shows the schematic reflection spectra of optical elements 202-205 depicted for current implementation. To anyone skillful in the art other spectral wavelengths can achieve similar spectral separation effect for keratometer. For example the fixation light can be in visible or NIR range of light.

Figure 3:
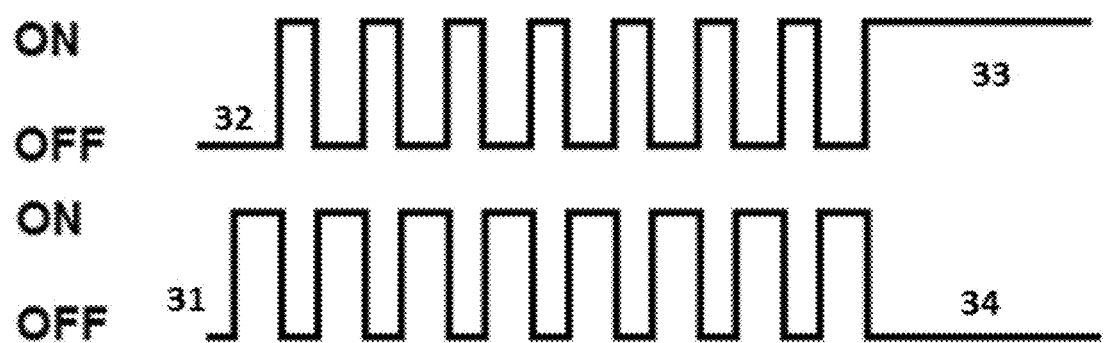
FIG. 3 depicts that counter-phase operation of Placido ring (with signal 31) and Fixation light for "NIR Red Reflex" illumination (with signal 32) shall allow both 23 and λ4 to pass to video camera. As a result, when Placido ring is off at stage 34, the NIR beam remains ON at stage 33 and can be used for "NIR Red Reflex" imaging of IOL and cataract by video camera.

During keratometer measurement one can turn on Placido ring 104 and Fixation light 107 in counter phase mode, as shown in FIG. 3. This way Placido ring image (Purkinje image) will not have an image of a bright spot from the Fixation light 107. Moreover, after measurement is completed Fixation light 107 remains on, providing a strong on-axis NIR or Visible beam to create a "red reflex" effect on the keratometer video camera 110 for better IOL (intraocular lens) imaging during IOL alignment or cataract visualization during its removal procedure. The "red reflex" effect is achieved when illumination of light source is reflected by patient's fundus and creating back illumination of cataractous lens or IOL for a better visibility and high contrast. Correspondingly various digital image enhancement methods are applied to live video of keratometer video camera 110 to outline IOL features for IOL alignment ease. This is done by a processor or a tablet PC. As shown in FIG. 3, counter-phase operation of Placido ring 104 with signal 31 and Fixation light 107 with signal 32 for "NIR Red Reflex" illumination shall allow both $\lambda_3$ and $\lambda_4$ to pass to video cameral 10. As a result at stage (33) in the figure, when LED ring is off (at stage 34) the NIR beam can be used for "NIR Red Reflex" imaging of IOL and cataract by video camera. The counter-phase operation of Placido ring and Fixation light for "NIR Red Reflex" illumination temporarily separates their ON time and allows pure NIR light ON time to support fixation detection. Red Reflex beam wavelength could also be Far Red $\lambda_3 \geq 530$ nm to provide visible back illumination of IOL for surgeon, when looking through the microscope 101.

Figure 4:
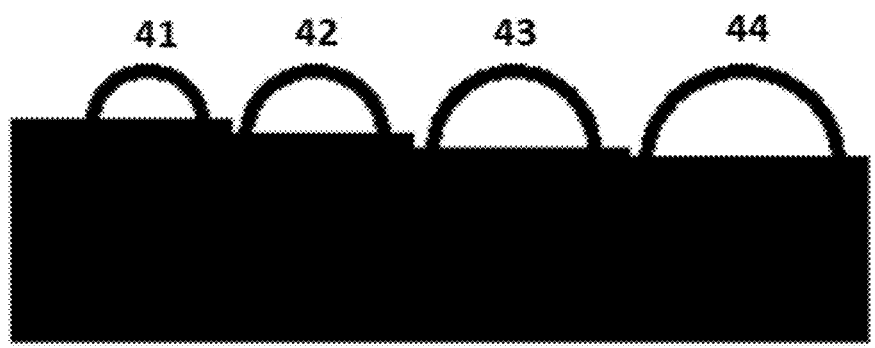
FIG. 4 depicts calibration fixture for several calibrated diameter metal balls (41-44) held at the same top height level, so that no microscope refocusing is required during calibration.
Figure 5:
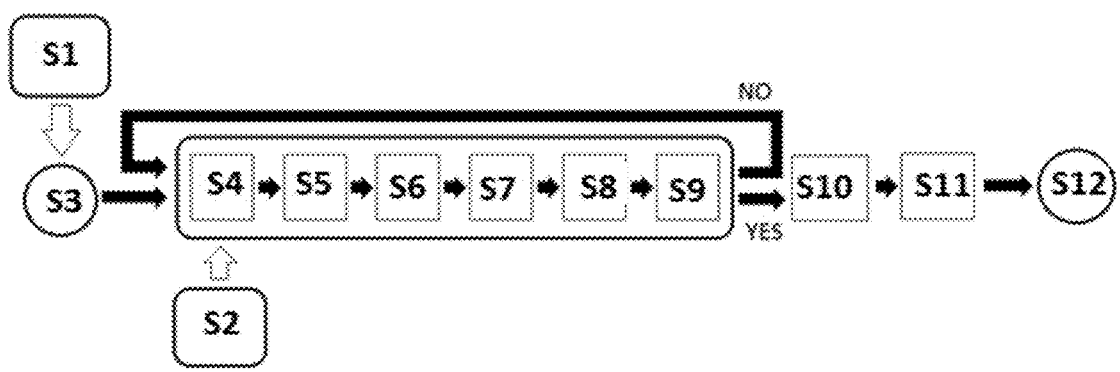
FIG. 5 depicts an intra-surgery keratometry method and a process flow as a block scheme in these steps: S1. Pre-operative biometry; S2. Keratometer calibration; S3. Cataract removal; S4. Eye preparation; S5. Microscope centration; S6. Microscope height adjustment; S7. LEDs brightness adjustment; S8. Achieving patient's fixation; S9. Measurement; S10. Displaying astigmatism line; S11. Toric IOL alignment; S12. Finishing cataract surgery.

FIG. 4 shows the schematic of a Calibration device for the keratometer device. Calibration fixture mounts several precision diameter metal balls (41-44). Current implementation has 4 balls of ranging diameter: 1.000 inches, 0.875 inches, 0.750 inches and 0.675 inches. The diameters of balls are chosen to cover range of human cornea curvatures. To have top point of each ball at the same elevation a step-like base is employed. The same height level is needed so that no microscope refocusing is done during calibration and constant camera magnification maintained. The calibration mode of Keratometer requests consecutively balls of different size and records Placido ring images of them. This allows to build a Calibration curve, where any diameter of camera image of Placido ring can be directly converted into radius of curvature of the surface that has produced Purkinje-1 image of Placido ring FIG. 5 depicts intra-surgery keratometry method and flow as a block scheme. The success of intra-surgery keratometry is dependent on adhering to these process steps, resulting in the accurate keratometry reading.

S1: Pre-operative biometry. This can be ultrasonic or optical imaging. Typically the important ocular biometry parameters needed to prescribe intra-ocular lens are Axial Length AL, corneal curvatures Ks, Astigmatism angle A, Anterior Chamber Depth ACD and some others.

S2: Microscope mounted keratometer calibration. This is done using the calibration fixture depicted in FIG. 4 or similar. Precision diameter balls are presented of several diameters in the range of 0.5-1.0 inches. The Placido ring images of different precision diameter balls are analyzed for ring diameters and calibration curve is generated.

S3: Cataract removal (phaco-emulsification or femto-laser). This involves all usual cataract surgery steps starting with incisions and up to lens material removal and capsule polishing.

S4: Eye preparation. Before keratometry measurement can be done on the patient's eye intra-ocular pressure is lowered to about 20-30 mmHg. Preferably this needs to be done using contact tonometers. After IOP is lowered the corneal incisions are closed by moderate hydration. Excessive hydration may distort corneal shape and Ks readout.

S5: Microscope centration with patient's eye. Rough centration can be performed by moving microscope optics laterally in X and Y coordinates. Fine alignment can be performed by clicking on keratometry square Region-of-Interest (ROI) on keratometer GUI touch screen and dragging it to center with Placido ring Purkinje-1 image.

S6: Microscope height adjustment is performed at maximum magnification. This is an important step, because Keratometry reading is directly affected by height. Because Depth-of-Field (DOF) of microscope is very shallow at maximum magnification—this is used for precision height positioning during calibration and keratometry measurement. The surgeon is requested to go to maximum magnification and focus on corneal apex to match with calibration ball apex height. This places microscope and keratometer height close to height used in calibration.

S7: Placido ring brightness adjustment for best image quality. This is done automatically by software after surgeon presses a "Measure" button. Manual option is available too.

S8: Achieving patient's fixation on blinking fixation light. Patient is asked to look at blinking visible light at the top. The fixation detector confirms patient's compliance and performs keratometry readings only in the moments of patient fixation compliance.

S9: Measurement—grabbing Placido ring Purkinje-1 reflection images (typically 6-500). The Calibration curve obtained in the calibration step is then used to calculate corneal Radii and K-values. Check if error is below the set limit—typically 0.25 Diopters of corneal curvature or less. If "YES," proceed with next step. If "NO," return to step S4.

S10: Displaying astigmatism line superimposed over patient's eye. This line is used as guidance for toric IOL alignment by surgeon.

S11: Maximizing Red Reflex illumination for best toric IOL alignment. IOL is implanted and toric IOL alignment is performed by matching IOL marks with digital marks, designating astigmatism angle.

S12: Finishing cataract surgery. All further steps of cataract surgery are performed that typically follow IOL implantation.

Figure 6:
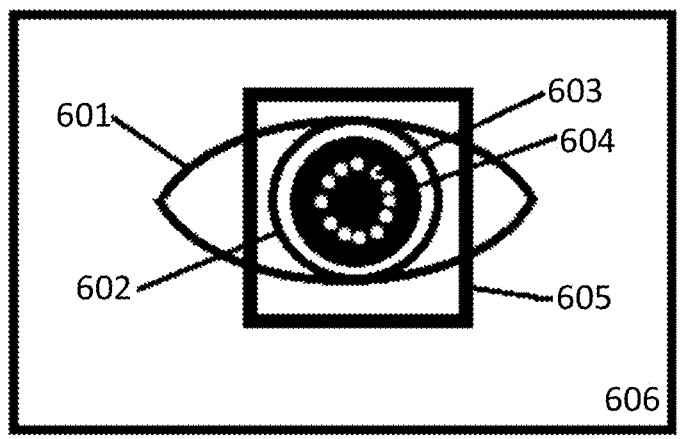
FIG. 6 depicts the concept of CMOS windowing for speeding up frames-per-second of Placido rings image acquisition.

When the keratometer is operated in an "Alignment Mode" during X-Y alignment of microscope and detachable keratometer with patient's eye, the video camera is running in a full frame setting to cover a wide field-of-view. Once the alignment is done, the keratometer can be switched to a "Measurement Step." By switching to a camera "windowing" mode during Measurement step one can obtain dramatically more measurements at faster speed and thus improve overall measurement accuracy. FIG. 6 depicts the concept of Video camera windowing for speeding up frames-per-second of Placido rings image acquisition. The schematic depiction is of patient's eye 601, limbus 602, Purkinje-1 reflection of Placido ring 603 on cornea, pupil 604 and Region-Of-Interest (ROI) 605. Video camera sensors have an ability to record just a small rectangular "window" 605 of full video frame 606. For a reasonable Purkinje images resolution ROI size should be 100×100 pixels or larger. A modern CMOS camera can have 40 Mega Pixel resolution –40,000,000 pixels in full frame. Thus a 100×100=10,000 pixel ROI will constitute 10,000/40,000,000=0.00025 of total frame area or 0.025%. The small rectangular "window" 605 can be 0.02%-60%, 0.02%-30%, 5-50%, 5-40%, 10-30%, or 15-25% of full video frame 606. At 30% the ROI area is 10× smaller than full frame and camera frames-per-second speed increases by approximately 10-fold. The time of such "window" recording is significantly shorter than full frame recording time. Thus switching to windowing mode speeds up frames-per-second speed of ROI recording many times. This is used to drastically increase number of frames within a time reasonable for intra-surgery keratometry—below 5 seconds—and increase measurement accuracy by increasing number of repeated measurements averaged for final result.

Figure 7:
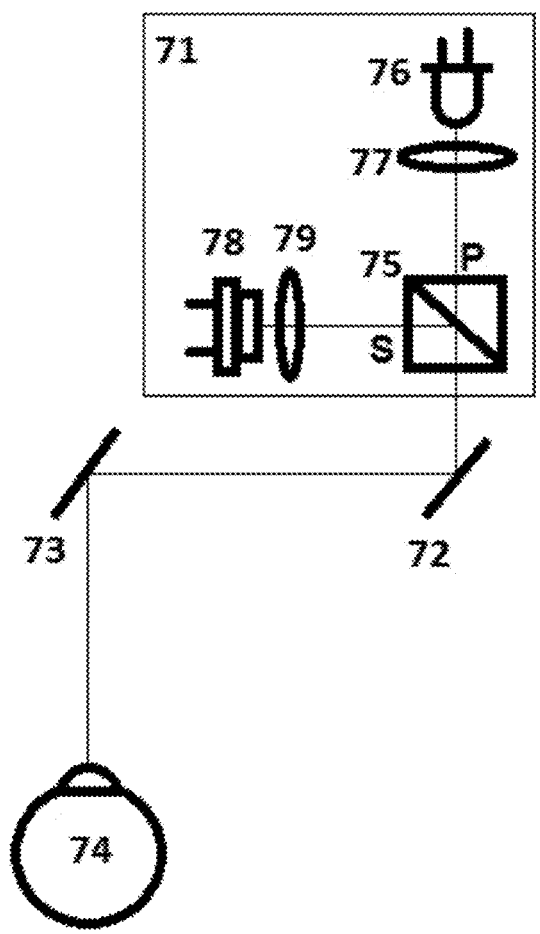
FIG. 7 depicts a fixation detector based on red fundus reflex in accordance of one embodiment of the present invention.

FIG. 7 depicts one embodiment of patient's eye fixation detector based on red fundus reflex. It is similar to red-eye effect in photos with flash. Human fundus reflects light most effectively in 500-700 nm. The reflection remains strong at 750 nm, but will become invisible to patient. One can use a source of light at 750 nm and measure the amount of light reflected back. This amount will depend on whether patient's eye visual axis is aligned with optical axis or not. Thus it can operate as fixation detector. In FIG. 7 fixation detector 71 is emitting light that is directed by beamsplitters 72 and 73 to patient's eye 74. Inside fixation detector a polarizing cube 75 is used to direct only p-polarized light to patient's eye. The light source 76 with collimating lens 77 directs a beam of near-collimated light to a polarizing beamsplitting cube 75. The strong cornea specular reflection will maintain S-polarization as it is reflected at normal incidence. Fundus has specular and scattered components of returning light. The scattered portion of light will be divided equally between S and P polarizations. Thus the P-polarized portion of fundus reflection will be reflected by polarizing beamsplitter cube 75 into detector 78 with collection lens 79. To make entire system more sensitive the source 76 can be pulsing at high frequency of 10 Hz to 1 MHz. The detector 78 will then have lock-in amplifier frequency filter circuitry to detect low level pulsing signal on top of regular light background. Another method of fixation monitoring is to measure the degree of circularity of pupil and limbus via camera image processing.

Figure 8:
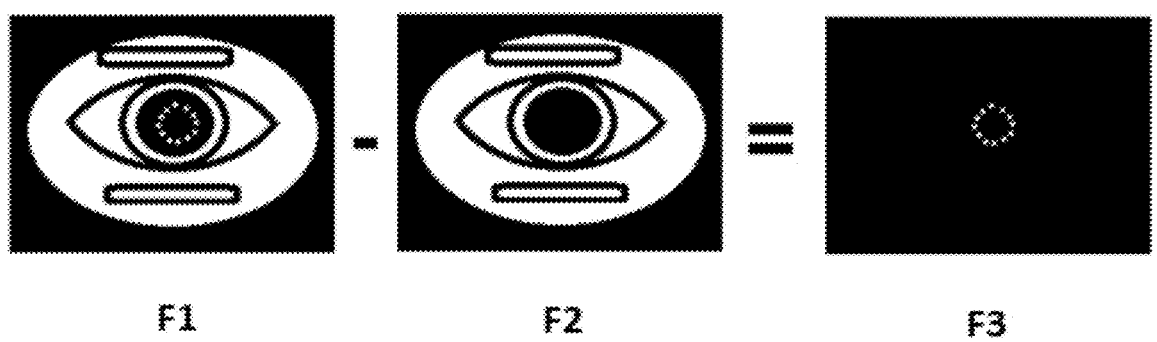
FIG. 8 explains pulsed light Placido ring keratometry for background subtraction.

FIG. 8 Explains pulsed light Placido ring keratometry for background subtraction. By pulsing the light source of Placido ring we can establish a mode where every second video frame taken is with Placido ring off. This will allow to subtract two consecutive frames for minimizing background light effect. One can also establish a mode where very third video, fourth video . . . $n^{th}$ video (n being the total number of frames) frame take is with Placido ring off as long as it allows to subtract two frames for minimizing background light effect. FIG. 8 shows frame F1 with Placido ring "ON" and frame F2 with Placido ring "OFF." When subtracting intensities of each pixel in frame F2 from frame F1 one obtains result—frame F3 that depicts mostly useful Placido ring signal. This makes system more stable to outside illumination. Also the dark background frame with Placido ring "OFF" can be taken with lower frequency, for example, every $10^{th}$ frame, or $100^{th}$ frame. This will yield more frames that contain useful image of Placido ring, and yet the background frame will be refreshed frequently enough to account for patient's eye movements.

Figure 9:
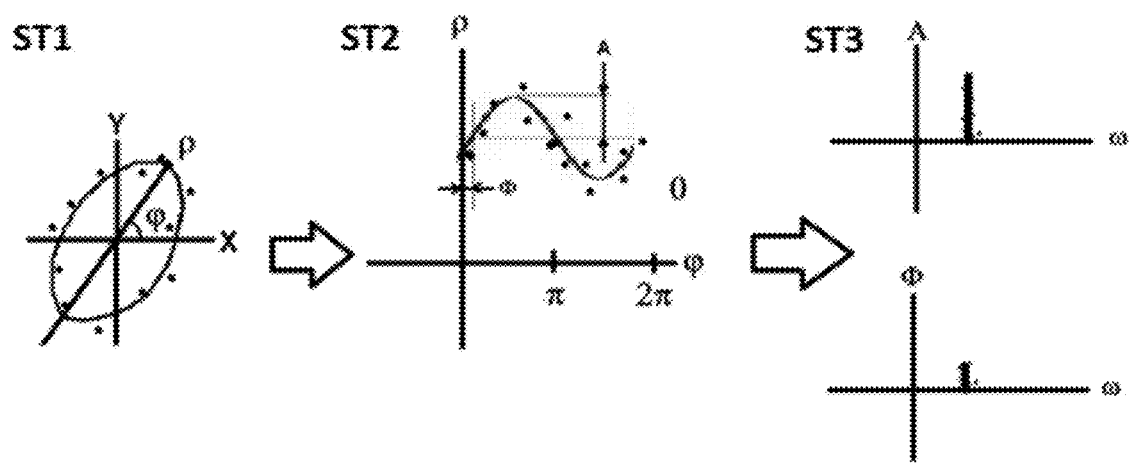
FIG. 9 explains Fourier analysis method applied to determine elliptical Purkinje-1 image parameters.

FIG. 9 Explains a Fourier analysis method applied to determine the refractive characteristics of the patient's eye. After identifying coordinates of all spots in Placido ring image one can average all Y and all X coordinates into $X_o$ and $Y_o$. Subtract $(X-X_0)$ and $(Y-Y_o)$ to center ellipse with coordinate system as shown in Step ST1. One can convert Cartesian system of coordinates X, Y into polar system of coordinates $\rho$, $\varphi$. When replotting all spots $\rho$, $\varphi$ in Cartesian plot one gets plot shown in Step ST2. Averaging all $\rho$ for all dots to $\rho_o$ and subtracting $\rho_o$ from all $\rho$-coordinates removes offset from zero. We have transformed our ellipse into sinusoidal plot in Step ST2. Applying Fast Fourier transform to the plot we can obtain amplitude A and phase angle $\Phi$. ($\rho_o$+A) and ($\rho_o$–A) give ellipse semi-major and semi-minor axis correspondingly. In Step ST3 these two parameters convert to slow and steep cornea radii (Ks) using calibration curve (established in S2 of FIG. 5.). And phase angle $\Phi$ gives ellipse angle and astigmatism angle of the patient's eye.

Figure 10:
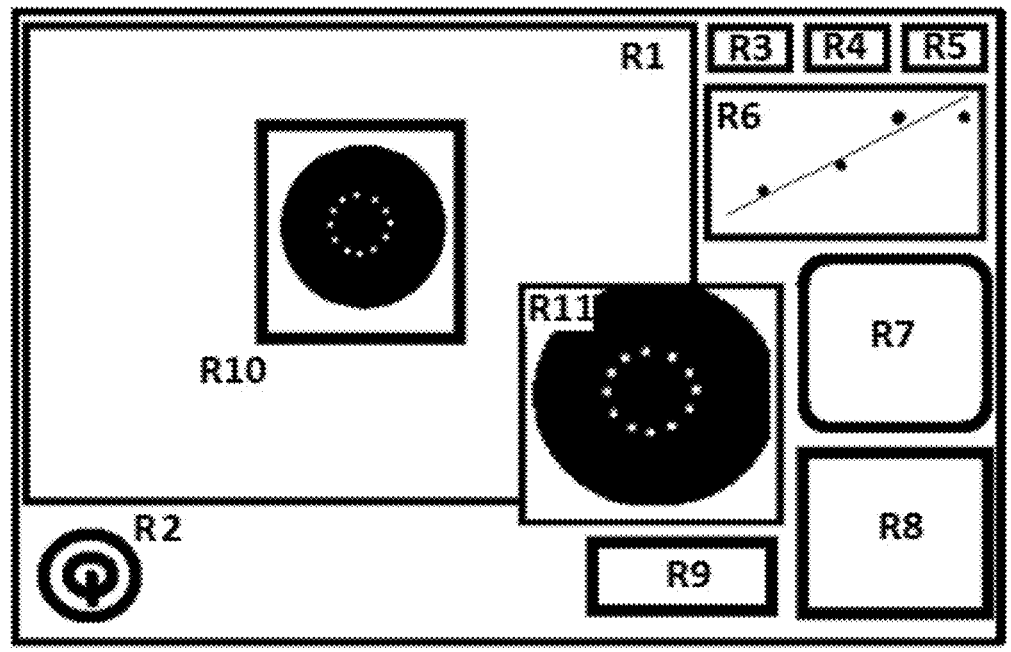
FIG. 10 depicts calibration GUI.

FIG. 10 depicts Calibration GUI. The full frame R1 is displayed for ease of microscope alignment. Region R2 depicts a button that switches the application off. Regions R3-R5 are for selecting Measurement, Calibration and Service modes. Calibration and Service modes are password protected. Graph R6 depicts calibration points and calibration curve. Region R7 is for selecting ball diameter currently in calibration. Region R8 is for illumination brightness controls. Region R9 is to select number of measurements to average for each data point. Region-Of-Interest containing calibration ball is displayed in window R11.

Figure 11:
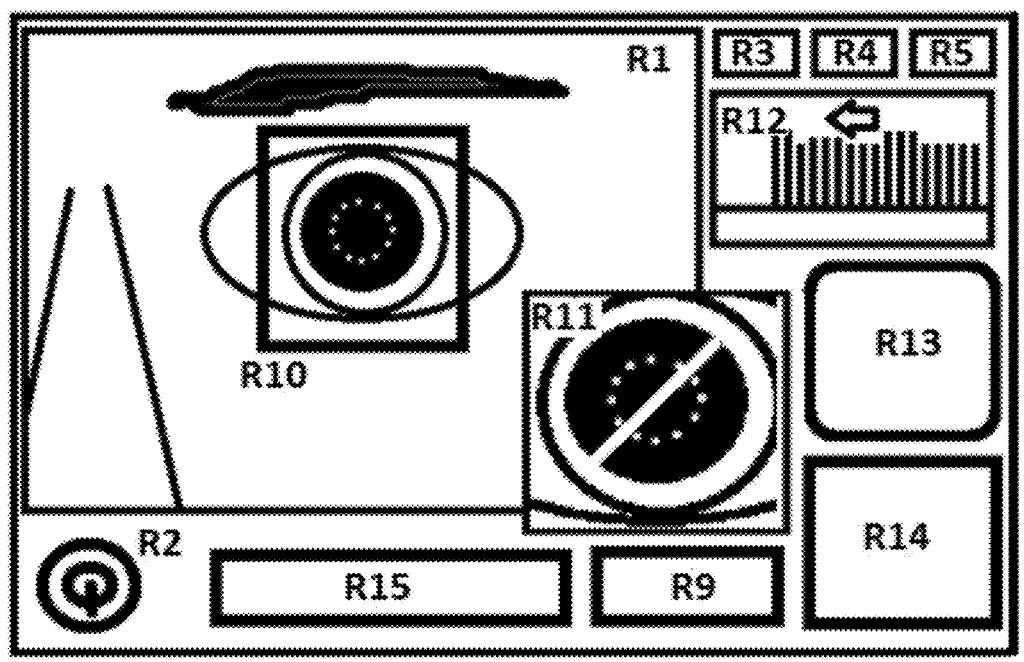
FIG. 11 depicts measurement GUI.

FIG. 11 depicts measurement GUI. The full frame R1 is displayed for ease of microscope alignment. Region R2 depicts a button that switches the application off. Regions R3-R5 are for selecting Measurement, Calibration and Service modes. Calibration and Service modes are password protected. Graph R12 depicts running chart of one measured keratometry parameter—K, Cylinder, Angle or other. Region R13 is for displaying keratometry measurement results. Region R14 is for inputting pre-operative biometry parameters such as Axial Length, Angular Offset of Anterior Angle with respect to Total Cornea Astigmatism and selecting IOL type and formula for prescription. Angular Offset of Anterior Angle with respect to Total Cornea Astigmatism is measured during office examination of the patient using instruments capable of Total Cornea measurement (anterior and posterior astigmatism combined). Region R9 is to select number of measurements to average. Region R15 is to display selected IOL prescription method. Region-Of-Interest containing patient's eye is displayed in window R11 and can be magnified in window R1. A press of a button on GUI switches from displaying full frame in window R1 to displaying zoomed in Region-Of-Interest. Provided Total Cornea (Anterior and Posterior Cornea) data are available and astigmatism angle of total cornea is different from astigmatism angle of anterior cornea by the amount of Delta—this amount can be an input in Measurement GUI to offset alignment guidance line angle by Delta.

Figure 12:
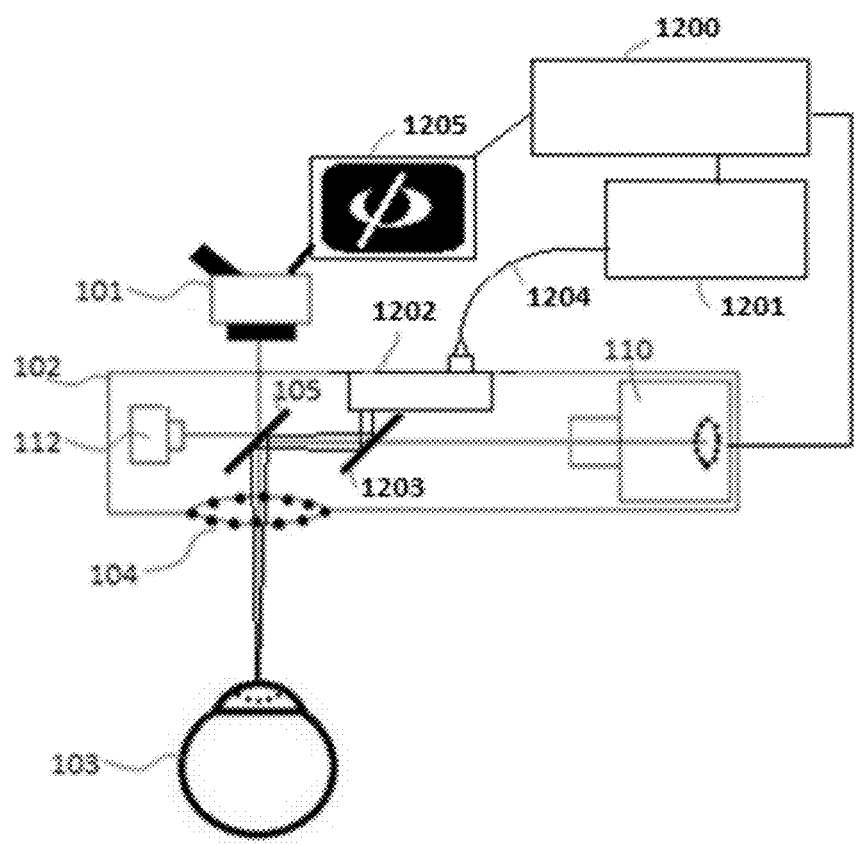
FIG. 12 depicts one detachable keratometer according to another embodiment of the present invention: 101—surgical microscope; 102—detachable keratometer; 103 procedure eye; 104—Placido ring light source; 105—Beamsplitter; 110—keratometer video camera with objective lens; 112—digital display with lens; 1200—processing unit; 1201—OCT laser and optics; 1202—OCT scanner; 1203—Beamsplitter; 1204—optical fiber; 1205—microscope mounted video monitor.

FIG. 12 depicts a combo of detachable microscope mounted keratometer and Optical Coherence Tomograph (OCT) scanner head. The two channels can be easily combined by the use of spectrally separated channels. Such OCT normally operates in 780 nm-900 nm, 1000 nm-1100 nm, 1250 nm-1400 nm, or 800 nm-1400 nm spectral range, while the Keratometer operates in NIR (700-900 nm) and Visible (400-700 nm) range. Thus complete spectral separation is possible of keratometer imaging channel and OCT imaging channels, as shown. The beamsplitter 1203 combines OCT and Keratometer optical paths—it reflects wavelengths over 900 nm and transmits NIR and Visible. A processing unit 1200 controls OCT laser and scanner. The OCT signal is transferred to OCT scanner over an optical fiber 1204. The results to guide surgeon can be displayed on the external video monitor 1205 mounted on the microscope or heads-up display 112, integrated into microscope vision system 101. Such addition of OCT allows for measuring posterior cornea refractive contributions and correct for them for better surgical outcomes. Also the location of implanted IOL can be controlled as effective lens position is a major contributing factor into cataract surgical outcomes. And lastly ocular Axial Length and Anterior Chamber Depth are measured with OCT.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

The invention claimed is:

1. A keratometer for intra-surgery measurements mounted under a surgical microscope, comprising:
    a Placido ring illuminating a patient's eye;
    a video camera;
    a beamsplitter directing a Purkinje image of the Placido ring to the video camera;
    a fixation light directing a beam for patient eye fixation, fixation confirmation or creating a red reflex effect to enhance IOL imaging and cataract visualization;
    a processor configured to determine the refractive characteristics and keratometer parameters of the patient's eye and to outline IOL features to help IOL alignment; and
    a digital display displaying the keratometer parameters and surgical guidance information for a surgeon,
    wherein 0.02-30% of the Purkinje image is defined as a small Region-of-Interest window and is used to extract information on the Purkinje image for high frames-per-second measurement and averaging.

2. The keratometer of claim 1, wherein the Placido ring is configured to flash with a frames-per-second rate of the video camera and to skip flashing for at least one frame for background recording and subtraction.

3. The keratometer of claim 1 further comprising a fixation detector,
    wherein the fixation light is an integrated fixation near-collimated visible or NIR light source pulsating at 0.5 Hz-1 MHz frequency; and
    the fixation detector confirms patient compliance and accepts measurements with correct fixation.

4. The keratometer of claim 1 further comprising an integrated optical coherence tomography scanner,
    wherein the integrated optical coherence tomography scanner extracts information on posterior corneal surface curvature, anterior chamber depth and IOL location.

5. The keratometer of claim 1, wherein the digital display is integrated into the keratometer as a digital overlay display.

6. The keratometer of claim 3, wherein the near-collimated visible or NIR light source, when operated in a constant "ON" mode, creates a fundus reflection effect for video contrast.

7. The keratometer of claim 6, wherein the digital image enhancement method is applied to live video to outline cataractous lens and IOL features for IOL alignment ease.

8. The keratometer of claim 3, wherein different optical channels of the microscope, Placido ring, the fixation light, the fixation detector and the Purkinje image are separated spectrally for a coaxial operation.

9. The keratometer of claim 1, wherein an angular offset in degrees is applied to compensate for difference between anterior corneal astigmatism and total cornea astigmatism, and combining anterior and posterior corneal astigmatism is applied in GUI.

10. A keratometry method comprising:
    receiving, from a video camera of a keratometer mounted under a surgical microscope, Purkinje images and a background image of a patient's eye by properly controlling a Placido ring and a fixation light;
    executing, by a processor, an analytic software to determine refractive characteristics and keratometer parameters of the patient's eye based on the Purkinje images and background image and a digital image enhancement method to outline IOL features to assist IOL alignment;
    displaying live lines over image of the patient's eye indicating a determined astigmatism angle of the eye; and
    capturing 0.02-30% of the Purkinje images by the video camera for high frames-per-second measurements and averaging.

11. The keratometry method of claim 10, wherein the Placido ring flashes with a frames-per-second rate of the video camera and skip flashing for at least one frame for background recording and subtraction.

12. The keratometry method of claim 10, wherein different optical channels are separated spectrally for a coaxial operation.

13. The keratometry method of claim 10 further comprising:
    providing an integrated fixation near-collimated visible or NIR light source pulsating at 0.5 Hz-1 MHz frequency and a fixation detector to confirm patient compliance; and
    accepting measurements with correct fixation.

14. The keratometry method of claim 10 further comprising:
    using Purkinje 1, 2, 3 and 4 images and/or integrated an optical coherence tomography scanner to extract information on posterior corneal surface curvature, anterior chamber depth and IOL location.

15. The keratometry method of claim 10 further comprising using precision diameter balls of known sizes for calibration.

16. The keratometry method of claim 10, wherein the analytic software is configured to calculate an astigmatism angle by offsetting to account for a pre-op total cornea astigmatism angle delta.

17. The keratometry method of claim 10 further comprising providing a near-collimated visible or NIR light source to fix the patient's eye and creating a red reflex effect enhancing the contrast of a IOL or assisting cataract visualization.

18. The keratometry method of claim 10, wherein the refractive characteristics and the live lines are displayed in a tablet PC, an external display attachable on the surgical microscope, or a digital display integrated with the keratometer injecting digital overlay into a surgeon's intra-operative view.

19. The keratometry method of claim 10, wherein the analytic software applies a Fast Fourier Transformation to analyze the Purkinje image for ellipse parameters extraction.

20. The keratometry method of claim 10 further comprising the following steps:
    pre-operative biometry,
    keratometer calibration,
    cataractous lens surgical removal,
    eye preparation for intra-operative keratometry,
    microscope centration,
    microscope height adjustment,
    LEDs brightness adjustment, achieving patient's fixation,
keratometry measurement,
displaying astigmatism line, and
toric IOL implantation and alignment.

* * * * *